United States Patent
Kuhn et al.

(10) Patent No.: US 10,337,977 B1
(45) Date of Patent: Jul. 2, 2019

(54) SYSTEMS AND METHODS FOR GLASS PARTICLE DETECTION

(71) Applicant: CORNING INCORPORATED, Corning, NY (US)

(72) Inventors: David Joseph Kuhn, Prattsburgh, NY (US); Philip Robert LeBlanc, Corning, NY (US); Robert Arthur McIntosh, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 15/818,324

(22) Filed: Nov. 20, 2017

Related U.S. Application Data

(60) Provisional application No. 62/425,277, filed on Nov. 22, 2016.

(51) Int. Cl.
| | |
|---|---|
| *G01N 21/00* | (2006.01) |
| *G01N 15/14* | (2006.01) |
| *G01N 21/85* | (2006.01) |
| *G01N 21/892* | (2006.01) |
| *G01N 21/89* | (2006.01) |

(52) U.S. Cl.
CPC ......... *G01N 15/1434* (2013.01); *G01N 21/85* (2013.01); *G01N 21/892* (2013.01); *G01N 21/8914* (2013.01)

(58) Field of Classification Search
CPC ...... G01N 21/53; G01N 21/51; G01N 21/532; G01N 15/1434; G01N 15/0205
USPC .......................................................... 356/339
See application file for complete search history.

(56) References Cited

U.S. PATENT DOCUMENTS

| | | | |
|---|---|---|---|
| 2,649,500 | A | 8/1953 | Fedorchak |
| 6,404,489 | B1 | 6/2002 | Yu |
| 7,307,714 | B2 | 12/2007 | Cyr et al. |
| 8,803,968 | B2 | 8/2014 | Kim et al. |

(Continued)

FOREIGN PATENT DOCUMENTS

| | | |
|---|---|---|
| CN | 201795992 U | 4/2011 |
| JP | 2005017003 A | 1/2005 |

(Continued)

OTHER PUBLICATIONS

Jiancheng Jia, "A Machine Vision Application for Industrial Assembly Inspection", 2009 Second International Conference on Machine Vision. DOI 10.1109/ICMV.2009.51, pp. 172-176.

(Continued)

*Primary Examiner* — Md M Rahman
(74) *Attorney, Agent, or Firm* — Dinsmore & Shohl LLP

(57) ABSTRACT

A particle detection system includes a light source configured to emit a light beam into a cylindrical glass article when the cylindrical glass article is imaged by the glass particle detection system. The light beam is directed along a beam propagation axis that is perpendicular to a longitudinal axis of the cylindrical glass article. The particle detection system further includes a first polarizer positioned between the light source and the cylindrical glass, a camera configured to capture an image of the light beam reflected from the cylindrical glass article, and an analyzer positioned between the cylindrical glass article and the camera. An optical axis of the camera is perpendicular to the beam propagation axis of the light source.

14 Claims, 10 Drawing Sheets

(56) References Cited

U.S. PATENT DOCUMENTS

| | | | |
|---|---|---|---|
| 9,842,408 B2* | 12/2017 | Milne | G01N 21/9027 |
| 9,922,429 B2* | 3/2018 | Milne | G01N 21/9027 |
| 2015/0346109 A1* | 12/2015 | Fontaine | G01N 21/89 |
| | | | 356/239.8 |

FOREIGN PATENT DOCUMENTS

| | | |
|---|---|---|
| JP | 2009186281 A | 8/2009 |
| KR | 20150071228 A | 6/2015 |

OTHER PUBLICATIONS

Syringe Inspection, Glass International Jul./Aug. 2005. vol. 28, Issue 4. p. 7.

* cited by examiner

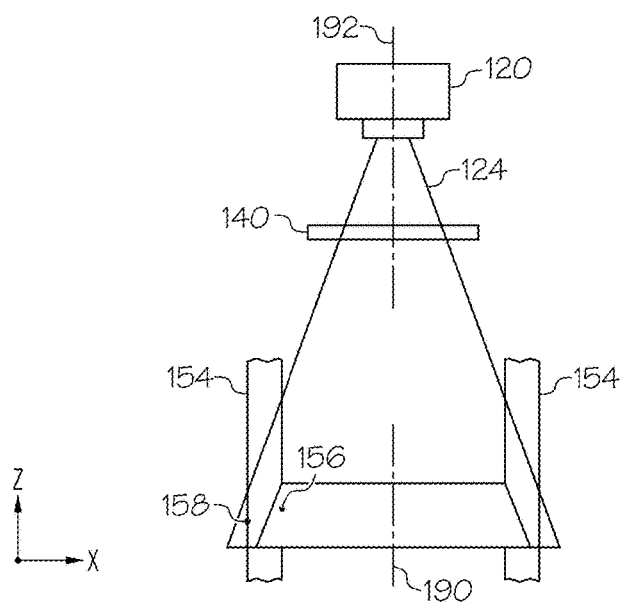
FIG. 2A
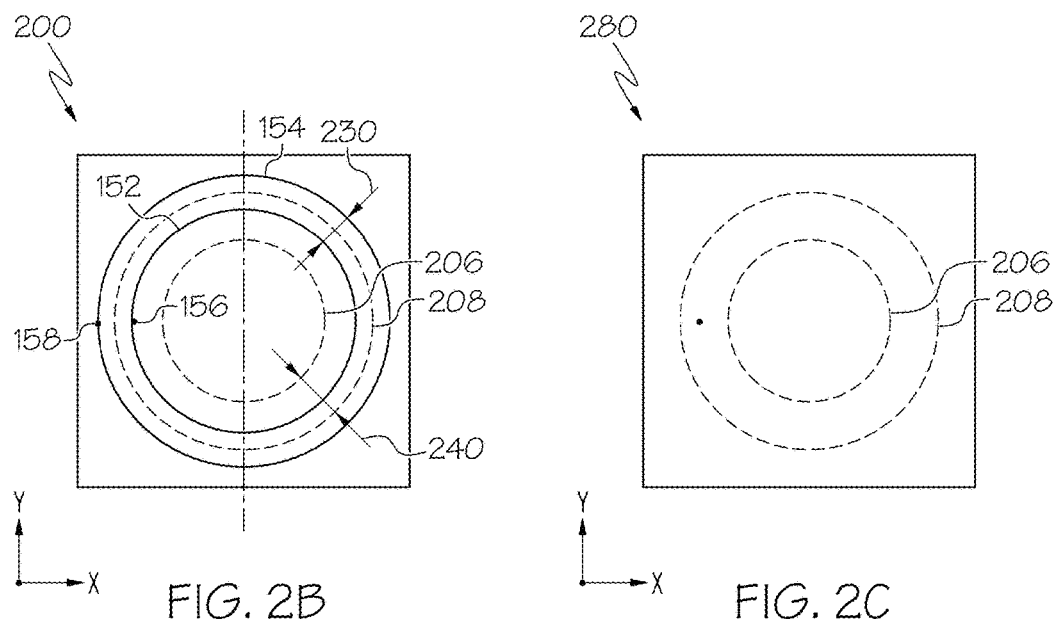
FIG. 2B
FIG. 2C

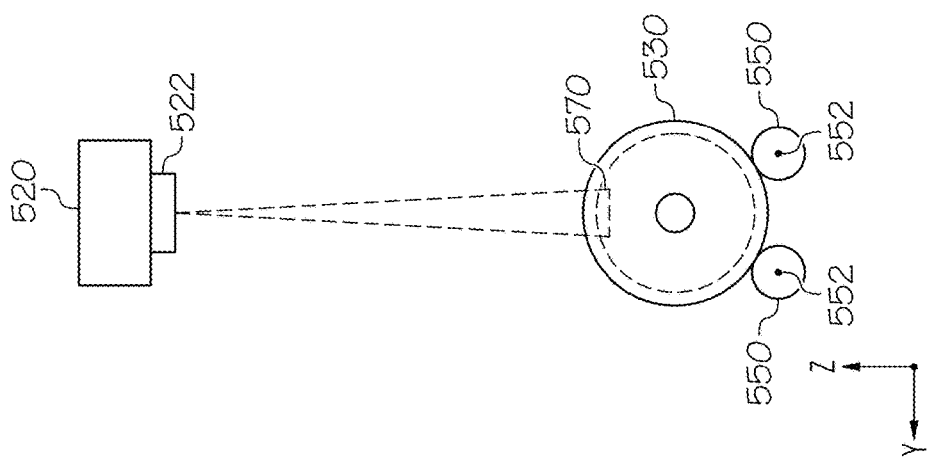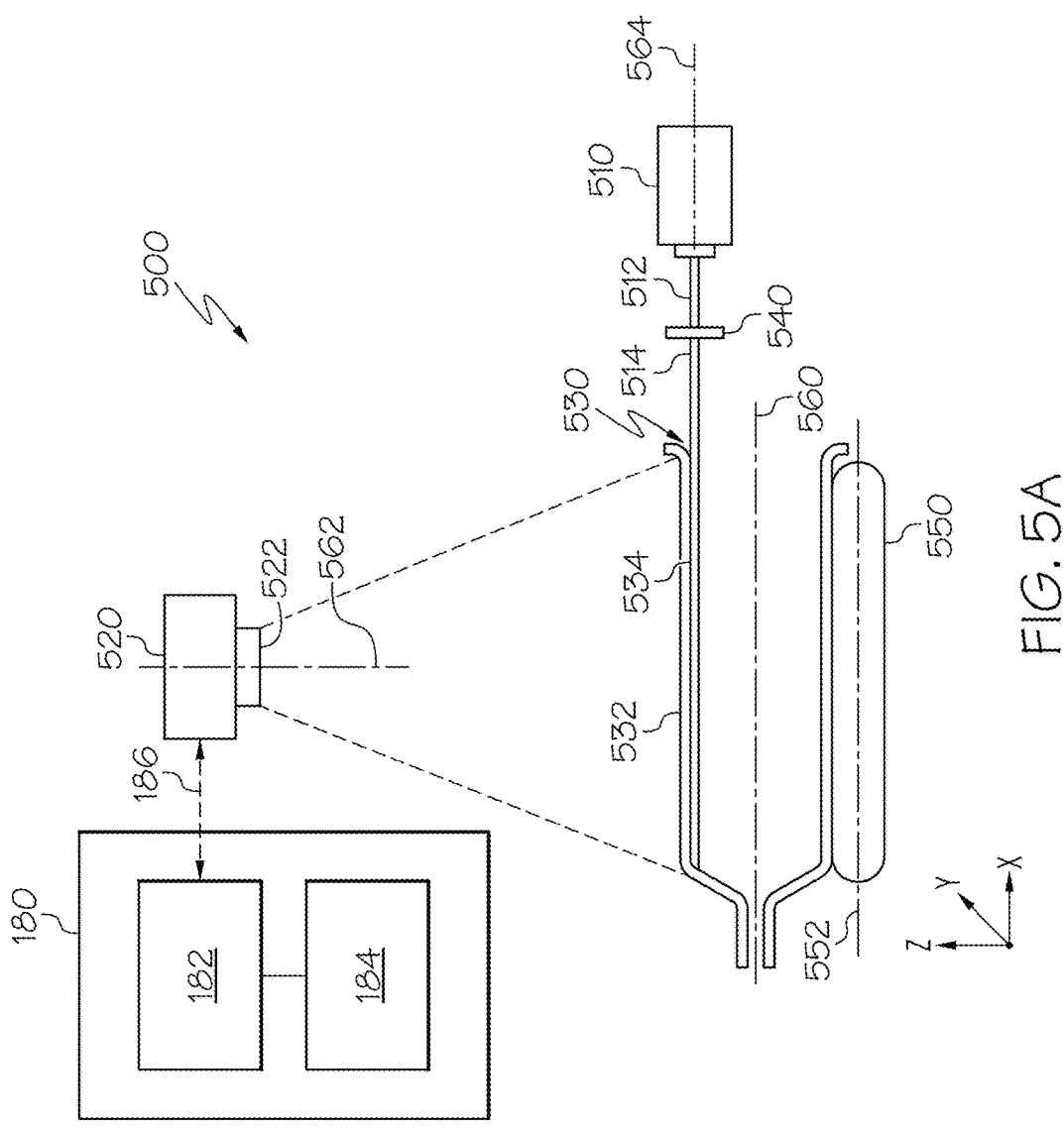

SYSTEMS AND METHODS FOR GLASS PARTICLE DETECTION

CROSS-REFERENCE TO RELATED APPLICATION(S)

This application claims priority to U.S. Provisional Patent Application No. 62/425,277, filed on Nov. 22, 2016, the entire contents of which are herein incorporated by reference.

BACKGROUND

Field

The present specification generally relates to detecting glass article defects and, more particularly, to detecting particles on inner surfaces of cylindrical glass articles.

Technical Background

The manufacture of glass tubing products (e.g., tubes, syringes, and vials) for use in the pharmaceutical industry sometimes leads to particles or fibers that adhere to the exposed surfaces of the glass tubing products. For example, particles may be attached to the inner wall or the outer wall of the glass tubing products. Fiber and particle defects of this type are a result of the converting process that involves scoring of a long cylindrical tube to produce smaller individual parts. These defects may be particularly undesirable if they are on the inside of a syringe where they might come loose and contaminate the medical product contained with the syringe or even be injected to a human body. This type of defect was responsible for over 25% of FDA recalls since 2013 and is a major source of lot yield loss in the industry.

Accordingly, alternative glass defect detection systems are desired.

SUMMARY

According to one embodiment, a particle detection system includes a light source configured to emit a light beam into a cylindrical glass article when the cylindrical glass article is imaged by the glass particle detection system. The light beam is directed along a beam propagation axis that is perpendicular to a longitudinal axis of the cylindrical glass article. The particle detection system further includes a first polarizer positioned between the light source and the cylindrical glass, a camera configured to capture an image of the light beam reflected from the cylindrical glass article, and an analyzer positioned between the cylindrical glass article and the camera. An optical axis of the camera is perpendicular to the beam propagation axis of the light source.

According to another embodiment, a method for detecting particles on a cylindrical glass article includes directing a light beam through a first polarizer into the cylindrical glass article along a beam propagation axis that is perpendicular to a longitudinal axis of the cylindrical glass article, the light beam polarized by the first polarizer producing light scattered by one or more particles on the inner wall of the cylindrical glass article, capturing, by a camera having an optical axis perpendicular to the beam propagation axis, an image of the light beam reflected from the cylindrical glass article including the scattered light via an analyzer, the analyzer located between the cylindrical glass article and the camera, and a polarization axis of the first polarizer being oriented at about 90 degrees relative to a polarization axis of the analyzer, and determining whether a particle is present in the image.

According to another embodiment, a glass particle detection system includes a light source configured to emit a light beam into a cylindrical glass article when the cylindrical glass article is imaged by the glass particle detection system, the light beam being directed along a beam propagation axis that is parallel to a longitudinal axis of the cylindrical glass article and illuminating an inner wall of the cylindrical glass article, and a camera configured to capture an image of the light beam, an optical axis of the camera being perpendicular to the beam propagation axis of the light source, a focal plane of the camera being located proximate to the inner wall of the cylindrical glass article.

According to another embodiment, a method for detecting particles on a cylindrical glass article includes directing, by a light source, a light beam into the cylindrical glass article along a beam propagation axis that is parallel to a longitudinal axis of the cylindrical glass article, the light beam illuminating an inner wall of the cylindrical glass article, capturing, by a camera, an image of the light beam reflected from the cylindrical glass article, an optical axis of the camera being perpendicular to the beam propagation axis of the light source, and a focal plane of the camera being located proximate to the inner wall of the cylindrical glass article, and determining whether illumination from the cylindrical glass article is present within the image.

According to another embodiment, a glass particle detection system includes a light source configured to emit a ring light, the ring light being directed along a beam propagation axis that is perpendicular to a longitudinal axis of a cylindrical glass article when the cylindrical glass article is imaged by the glass particle detection system, a beam splitter configured to reflect the ring light and change a direction of the ring light to a direction parallel to the longitudinal axis of the cylindrical glass article, a center of the ring light reflected by the beam splitter being aligned with the longitudinal axis of the cylindrical glass article, a first polarizer positioned between the light source and the beam splitter, a camera configured to capture an image of the ring light reflected from the cylindrical glass article, an optical axis of the camera being parallel with the longitudinal axis of the cylindrical glass article, and an analyzer positioned between the cylindrical glass article and the camera.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 2A depicts a partial side view of the glass particle detection system of FIG. 1 according to one or more embodiments shown and described herewith;

FIG. 2B depicts an image of light scattered from glass particles according to one or more embodiments shown and described herewith;

FIG. 2C depicts the image of FIG. 2B after being processed according to one or more embodiments shown and described herewith;

FIG. 5A depicts a side view of a glass particle detection system according to one or more embodiments described and shown herewith;

FIG. 5B depicts a front view of a glass particle detection system of FIG. 5A according to one or more embodiments described and shown herewith;

DETAILED DESCRIPTION

Figure 1:
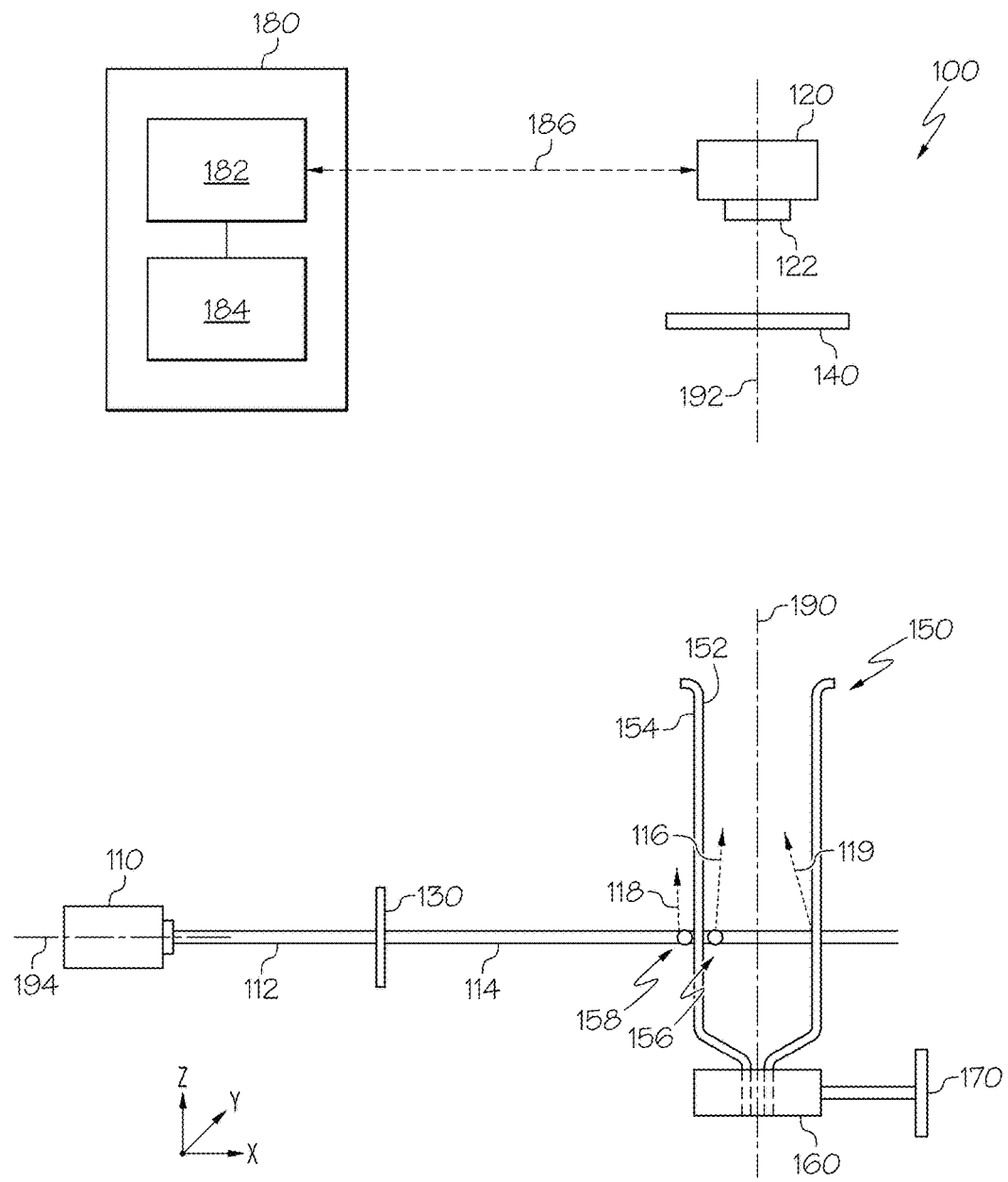
FIG. 1 schematically depicts a glass particle detection system according to one or more embodiments shown and described herein.

Reference will now be made in detail to various embodiments of systems and methods for detecting particles in cylindrical glass articles. Glass particles can be present on both the inner wall and the outer wall of the cylindrical glass articles. In some embodiments, only the presence of particles on the inner wall constitutes a reason for part rejection because particles on the inner wall of the cylindrical glass articles (e.g., tubes, syringes, vials) might come loose and contaminate the medical product inside the cylindrical glass article or even be injected to a human body. For this reason, a method for internal/external particle detection selectivity is desirable. One example of a glass particle detection system is schematically depicted in FIG. 1. The glass particle detection system may include a light source configured to emit a light beam into a cylindrical glass article. The light beam is directed along a beam propagation axis that is perpendicular to a longitudinal axis of the cylindrical glass article. The glass particle detection system further includes a first polarizer positioned between the light source and the cylindrical glass article, a camera configured to capture an image of the light beam reflected from the cylindrical glass article, and an analyzer positioned between the cylindrical glass article and the camera. An optical axis of the camera is perpendicular to the beam propagation axis of the light source. Various embodiments of glass particle detection systems and methods for detecting particles on the inner wall of a cylindrical glass article will be described in further detail herein with specific reference to the appended drawings.

One process for manufacturing cylindrical glass articles is the Vello process. The Vello process may be used to form cylindrical glass articles by flowing molten glass around a bell head of a known diameter while simultaneously flowing a gas, such as air, through the bell head. The bell head is positioned and supported within an opening of a glass delivery tank containing molten glass using a bell support. The bell support is also used to supply the gas to the bell head. The bell head, in conjunction with the flowing gas, forms the molten glass into cylindrical glass article with a desired wall thickness.

The high temperature of the molten glass may cause degradation of the metallic material of the bell support such as, for example, scaling, oxidation, and blistering. Particles resulting from the degradation of the metallic material may be carried through the bell support and bell head by the flowing gas and into the soft glass of the resulting cylindrical glass article. The particles may become embedded in the glass creating inclusion defects that may result in all or portions of the cylindrical glass article being discarded, decreasing manufacturing efficiencies and increasing manufacturing costs. The methods and systems described herein detect such particles. The systems and methods described herein may be used to detect defects on glass articles formed by the Vello process, or any other cylindrical glass article forming process.

FIG. 1 schematically depicts a glass particle detection system 100 according to one or more embodiments shown and described herein. The glass particle detection system 100 includes a light source 110, a camera 120, a polarizer 130, an analyzer 140, and a glass article 150. The glass article 150 may be a cylindrical glass article such as a tube, a syringe, a vial, etc. The glass article 150 has a longitudinal axis 190 which is parallel to the z axis in FIG. 1. The glass article is fixed to a holder 160 which is attached to a linear actuator 170.

The light source 110 may be a laser emitting a light beam 112. The light beam 112 may be a line light. The light source 110 may be a diode laser including an array of laser diodes which project a line of light. The light beam 112 may be directed along a beam propagation axis 194 that is perpendicular to the longitudinal axis 190 of the glass article 150. The light beam 112 may be orthogonal to a y-z plane in FIG. 1. In some embodiments, the light beam 112 may be directed in a direction not perpendicular to the longitudinal axis 190 of the glass article 150. For example, the light beam 112 may be directed at an angle of less than 90 degrees with respect to the longitudinal axis 190. In some embodiments, the width of the light beam 112 (in terms of the y direction of FIG. 1) may be larger than the outer diameter of the glass article shown in FIG. 2B such that the light beam 112 is projected on the whole cross section (parallel the x-y plane in FIG. 1) of the glass article 150. In some embodiments, the light source 110 is a light source other than a laser, such as an LED light source, a visible light source, an infrared light source, etc.

The polarizer 130 may be positioned between the light source 110 and the glass article 150 such that the light beam 112 from the light source 110 passes through the polarizer 130 at a normal direction of the polarizer 130 (i.e., +x axis direction). The polarizer 130 polarizes the non-polarized light beam 112 according to a polarization axis of the polarizer 130 and outputs a polarized light 114. The polarized light 114 may produce less glare when reflecting from the glass article 150 compared to the non-polarized light beam 112.

The glass article 150 may scatter the polarized light 114. The scattered polarized light may direct to various directions including a direction toward the camera 120. If the glass article 150 includes any particles on its surface, the polarized light 114 is scattered by the particles. In some embodiments as shown in FIG. 1, the glass article 150 may have an internal particle 156 attached on the inner wall 152 of the glass article 150 and an external particle 158 attached on the outer wall 154 of the glass article 150. The polarized light 114 may be scattered by the external particle 158 and the internal particle 156. The scattered light may direct to various directions including a direction toward the camera 120.

The polarization direction of the polarized light 114 is changed when the polarized light 114 is scattered by the external particle 158 or the internal particle 156. For example, the light 116 that was scattered by the internal particle 156 is polarized in a different direction than the polarization direction of the polarized light 114. Similarly, the light 118 that was scattered by the external particle 158 is polarized in a different direction than the polarization direction of the polarized light 114. In contrast, the polarization direction of the polarized light 114 is not changed when the polarized light 114 scatters on the glass article 150 where no particle is present. For example, the light 119 which was scattered by the glass article 150 is polarized in the same direction as the polarized light 114.

The analyzer 140 is positioned between the glass article 150 and the camera 120. The analyzer 140 may be a polarizer that polarizes an incident light. The analyzer 140 may have similar light optical characteristics (e.g., polarization) as the polarizer 130. The polarization axis of the analyzer 140 may be oriented to a different direction than the polarization axis of the polarizer 130. For example, the polarization axis of the analyzer 140 may be oriented at about ±90 degrees relative to the polarization axis of the polarizer 130. Thus, the polarized light 114 polarized according to the polarization axis of the polarizer 130 cannot pass through the analyzer 140 because the polarized light 114 is polarized in a direction orthogonal to the polarization axis of the analyzer 140. Similarly, the light 119 which was reflected from the glass article 150 cannot pass through the analyzer 140 because the light 119 is polarized in a direction orthogonal to the polarization axis of the analyzer 140.

In contrast, the light 118 that was scattered by the external particle 158 is polarized in a direction that is not orthogonal to the polarization axis of the polarized light 114. For example, the polarization direction of the light 118 may be different from the polarization axis of the polarizer 130, but not orthogonal to the polarization axis of the analyzer 140. Thus, a portion of the light 118 would pass through the analyzer 140 because the difference between the polarization direction of the light 118 and the polarization axis of the analyzer 140 is not 90 degrees, i.e., not orthogonal. Similarly, the light 116 that was scattered by the internal particle 156 is polarized in a direction that is not orthogonal to the polarization axis of the analyzer 140. For example, the polarization direction of the light 116 may be different from the polarization axis of the polarizer 130, but not orthogonal to the polarization axis of the analyzer 140. Thus, a portion of the light 116 would pass through the analyzer 140 because the difference between the polarization direction of the light 116 and the polarization axis of the analyzer 140 is not 90 degrees, i.e., not orthogonal. In this regard, only light that is scattered by particles on the outer wall 154 or the inner wall 152 of the glass article 150 can pass through the analyzer 140.

The camera 120 may capture an image of the light beam reflected from the glass article 150. The camera 120 may be any device having an array of sensing devices capable of detecting radiation in an ultraviolet wavelength band, a visible light wavelength band, or an infrared wavelength band. The camera 120 may have a focal plane that is located where the polarized light 114 overlaps with the glass article 150. The focal plane may be parallel to the x-y plane in FIG. 1. The camera 120 may include an optical lens 122. The camera 120 may capture an image of the light beam reflected from the glass article 150 including the external particle 158 and the internal particle 156, which is illustrated, for example, in FIG. 2A. The optical axis 192 of the camera 120 may be orthogonal to the beam propagation axis 194. The optical axis 192 of the camera 120 may be parallel with the longitudinal axis 190 of the glass article 150. In some embodiments, the optical axis 192 of the camera 120 may be co-located with the longitudinal axis 190 of the glass article 150. In another embodiment, the optical axis 192 of the camera 120 may not be parallel with the longitudinal axis 190 of the glass article 150, but the optical axis 192 may be crossed with the longitudinal axis 190 of the glass article 150 at a point proximate to the focal plane of the camera 120.

The linear actuator 170 may move in a vertical direction (+/−z direction) to move the glass article 150 in the vertical direction. As the linear actuator 170 moves glass article 150 in the vertical direction, the light source 110 can direct the polarized light 114 to the entire surface of the glass article 150. The camera 120 can also capture images of the light beam reflected from each and every portion of the wall of the glass article 150.

The camera 120 may communicate with a computing device 180 via a communication path 186. The computing device 180 may include one or more processors 182, and a memory module 184. Each of the one or more processors 182 may be any device capable of executing machine readable instructions. Accordingly, each of the one or more processors 182 may be a controller, an integrated circuit, a microchip, a computer, or any other computing device. The one or more processors 182 are coupled to the communication path 186 to communicate with the camera 120. The camera 120 may transmit the captured image of the light beam reflected from the glass article 150 to the processor 182 of the computing device 180 via the communication path 186. In some embodiments, the camera 120 may include the one or more processors 182 and the memory module 184. In some of such embodiments, the camera 120 may capture an image of the light beam, process the image by the one or more processors 182, and store the processed image in the memory module 184.

The communication path 186 may be formed from any medium that is capable of transmitting a signal such as, for example, conductive wires, conductive traces, optical waveguides, or the like. In some embodiments, the communication path 186 may facilitate the transmission of wireless signals, such as WiFi, Bluetooth, Near Field Communication (NFC) and the like. Moreover, the communication path 186 may be formed from a combination of mediums capable of transmitting signals. In one embodiment, the communication path 186 comprises a combination of conductive traces, conductive wires, connectors, and buses that cooperate to permit the transmission of electrical data signals to components such as processors, memories, sensors, input devices, output devices, and communication devices. Accordingly, the communication path 186 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The one or more memory modules 184 may comprise RAM, ROM, flash memories, hard drives, or any device capable of storing machine readable instructions such that the machine readable instructions can be accessed by the one or more processors 182. The one or more memory modules 184 may store images captured by the camera 120. The captured images may be processed by the one or more processors 182 before being stored in the one or more memory modules 184. The machine readable instructions may comprise logic or algorithm(s) written in any programming language of any generation (e.g., 1 GL, 2 GL, 3 GL, 4 GL, or 5 GL) such as, for example, machine language that may be directly executed by the processor, or assembly language, object-oriented programming (OOP), scripting languages, microcode, etc., that may be compiled or assembled into machine readable instructions and stored on the one or more memory modules 184. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components.

FIG. 2A depicts a partial side view of the glass particle detection system in FIG. 1 according to one or more embodiments shown and described herewith. The camera 120 may have a field of view 124 which extends beyond an outer wall 154 of the glass article 150. The camera 120 may have a depth-of-field that is one to five times larger than the thickness of the wall of the glass article 150. For example, the camera 120 may have a depth-of-field of 4 mm. The camera 120 has the optical axis 192 which may be parallel or co-located with the longitudinal axis 190 of the glass article 150.

FIG. 2B depicts an image of light reflected from the glass particles 156 and 158 according to one or more embodiments shown and described herewith. The camera 120 may have a field of view 124 which extends beyond the outer wall 154. In this embodiment, the image 200 illustrates a view of a focal plane of the camera 120. The image 200 may depict the inner wall 152 and the outer wall 154 of the glass article 150, a wall thickness 230 of the glass article 150, a region of interest 240, an internal particle 156 and an external particle 158.

The outer wall 154 and the inner wall 152 are illustrated in the image 200 in FIG. 2B for reference only, and the actual image may not include the outer wall 154 and the inner wall 152. As described above, because the polarization direction of the light scattered by particles is changed by certain degrees, the light scattered by the internal particle 156 and the external particle 158 can pass through the analyzer 140 and reach the camera 120. Thus, both the internal particle 156 and the external particle 158 may be visible to the camera 120, and included in the image 200.

The region of interest 240 may be defined by an inner circle 206 and an outer circle 208. The outer circle 208 may be located between the inner wall 152 and the outer wall 154 of the glass article 150. The inner circle 206 may be located inside the inner wall 152 of the glass article 150. The radius of the inner circle 206 may be set less than the radius of the inner wall 152. For example, the radius of the inner circle 206 may be about 90%-95% of the radius of the inner wall 152. In another example, the radius of the inner circle 206 may be about 80% of the radius of the inner wall 152. By defining the region of interest by the outer circle 208 and the inner circle 206, the external particle 158 may be located outside the region of interest 240 whereas the internal particle 156 may be located inside the region of interest 240. The indication of the region of interest 240 may be embedded to an actual image captured by the camera 120 in order to facilitate determining whether a particle is present on the inner wall of the glass article 150. In embodiments, the one or more processors 182 may determine whether any particle is present within the region of interest 240 of the image captured by the camera 120. If it is determined that a particle is present within the region of interest 240, the one or more processors 182 may determine that the particle is attached to the inner wall of the glass article 150. The one or more processors 182 may indicate that the glass article 150 should be rejected based on the determination. The indication of rejection may be stored in the one or more memory modules 184 along with the identification of the glass article 150. If it is determined that no particle is present within the region of interest 240, the one or more processors 182 may determine that no particle is present on the inner wall of the glass article 150. The determination may be stored in the one or more memory modules 184 along with the identification of the glass article 150.

FIG. 2C depicts the image of FIG. 2B after being processed according to one or more embodiments shown and described herein. The captured image 200 may be processed by the camera 120 to remove any illumination, noise, particles, etc. outside the region of interest 240 while maintaining content or illumination within the region of interest 240. In some embodiments, the camera 120 may send the captured image to the one or more processors 182 and the one or more processors 182 may implement image processing on the captured image to remove any illumination, noise, particles, etc. outside the region of interest. With this processing, the external particle 158 shown in the camera view is removed while the internal particle 156 remains in the region of interest 240. Then, the one or more processors 182 may determine whether any particle is present within the region of interest 240 on the processed image 280. If it is determined that a particle is present within the region of interest 240 on the processed image 280, the one or more processors 182 may determine that the particle is attached to the inner wall of the glass article 150. The one or more processors 182 may indicate that the glass article 150 should be rejected based on the determination. The indication of rejection may be stored in the one or more memory modules 184 along with the identification of the glass article 150. If it is determined that no particle is present within the region of interest 240 on the processed image 280, the one or more processors 182 may determine that no particle is present on the inner wall of the glass article 150. The determination may be stored in the one or more memory modules 184 along with the identification of the glass article 150.

In embodiments, various processing methods may be implemented on the captured image in order to remove undesirable data on the image. For example, a threshold filter may be applied to the captured image to remove most of the unwanted artifacts from the image. The processing may also convert the captured image to a binary image. For example, particles captured on the image may be converted to white dots whereas the rest of the image may be converted to black dots. A particle filter may be applied to the captured image to remove any artifacts that do not persist after image processing. The various processing may effectively remove features in the image that are too small to be real defects.

With respect to particles in the region of interest 240, the camera 120 or the one or more processors 182 may implement processing the image to enlarge the particles in the image relative to the background structure. For example, the internal particle 156 may be enlarged on the processed image 280. The enlargement processing is intentionally implemented to enhance the sensitivity of detecting particles. The actual particle size may be determined by applying a calibration to the image based on testing samples of known particle sizes.

Figure 3A:
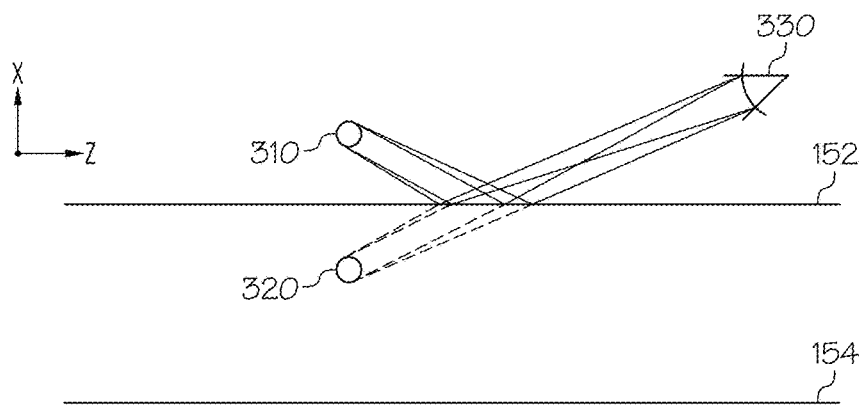
FIG. 3A depicts a ray diagram of an observer viewing a glass article including a particle on the inner wall of the glass article according to one or more embodiments shown and described herewith.

FIG. 3A depicts a ray diagram of an observer viewing the glass article 150 including a particle on the inner wall 152 of the glass article 150. In this embodiment, a particle 310 is attached on the inner wall 152 of the glass article 150. When an observer 330 sees the particle 310, the observer 330 not only directly sees the particle but also sees a virtual image of the particle 310. The virtual image 320 of the particle 310 is created due to a reflection of light on the inner wall 152. The particle 310 and the virtual image 320 have mirror symmetry across the inner wall 152. Because the particle 310 is attached on the inner wall 152 of the glass article 150, the virtual image 320 also appears to be attached on the inner wall 152 as shown in FIG. 3A.

Figure 3B:
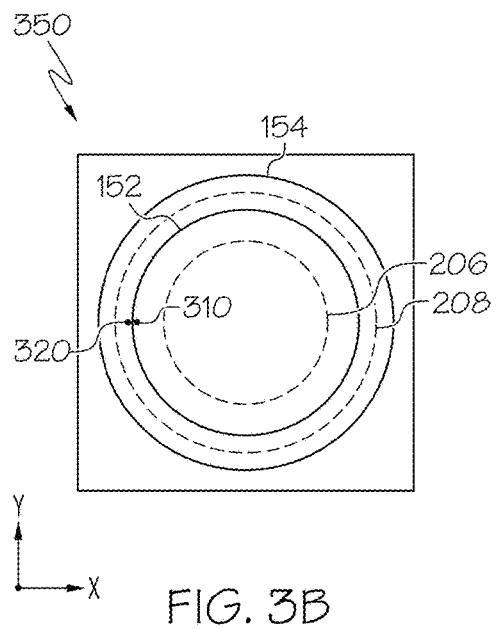
FIG. 3B depicts an image of a focal plane crossing the glass article including a particle according to one or more embodiments described and shown herewith.

FIG. 3B depicts an image of a glass article including a particle according to one or more embodiments described and shown herewith. As shown in FIG. 1, the image 350 is a view from the camera 120 with a focal plane where the polarized light 114 overlaps with the glass article 150. The indications of the inner wall 152 and the outer wall 154 are included in FIG. 3B for reference only, and the actual image 350 may not include the indications of the inner wall 152 and the outer wall 154. The optical axis 192 of the camera 120 may be aligned with the longitudinal axis 190 of the glass article 150. The particle 310 is shown to be attached on the inner wall 152 of the glass article 150 and the virtual image 320 is also shown to be attached to the inner wall 152. Both the particle 310 and the virtual image 320 are located within the region of interest 240 defined by the inner circle 206 and the outer circle 208.

The particle 310 and the virtual image 320 may have mirror symmetry across the inner wall 152 such that the particle 310 and the virtual image 320 appear to be attached to each other as shown in FIG. 3B. Because the mirror symmetry of a particle and a virtual image thereof attaching to each other is present only when a particle is attached on the inner wall 152 of the glass article 150, the mirror symmetry indication in an image captured by the camera 120 increases detectability of a particle on the inner wall 152 of the glass article 150. In addition, the cluster of a particle and a virtual image thereof increases detectability of the particle of the glass article 150.

Figure 3C:
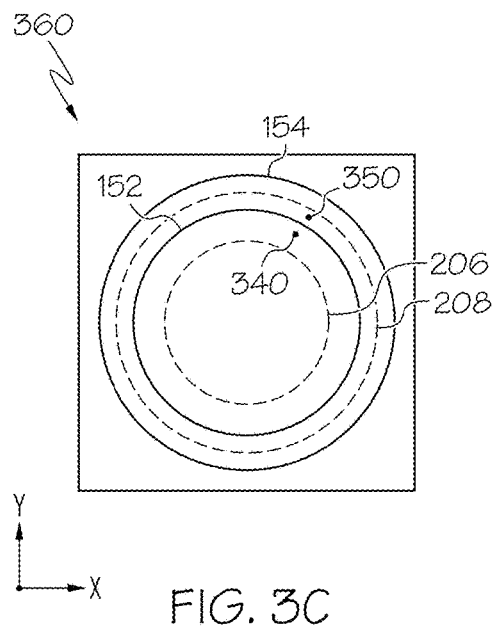
FIG. 3C depicts an image of a focal plane crossing the glass article including a particle according to another embodiment described and shown herewith.

When a particle and its virtual image are not attached to each other on an image, it may be determined that the particle is not attached on the inner wall 152 of the glass article 150. For example, as depicted in the image 360 of FIG. 3C, a particle 340 and a virtual image 350 of the particle 340 are located within the region of interest 240, but are not attached to each other. In this example, it may be determined that the particle 340 is not attached to the inner wall 152 of the glass article 150.

Figure 4A:
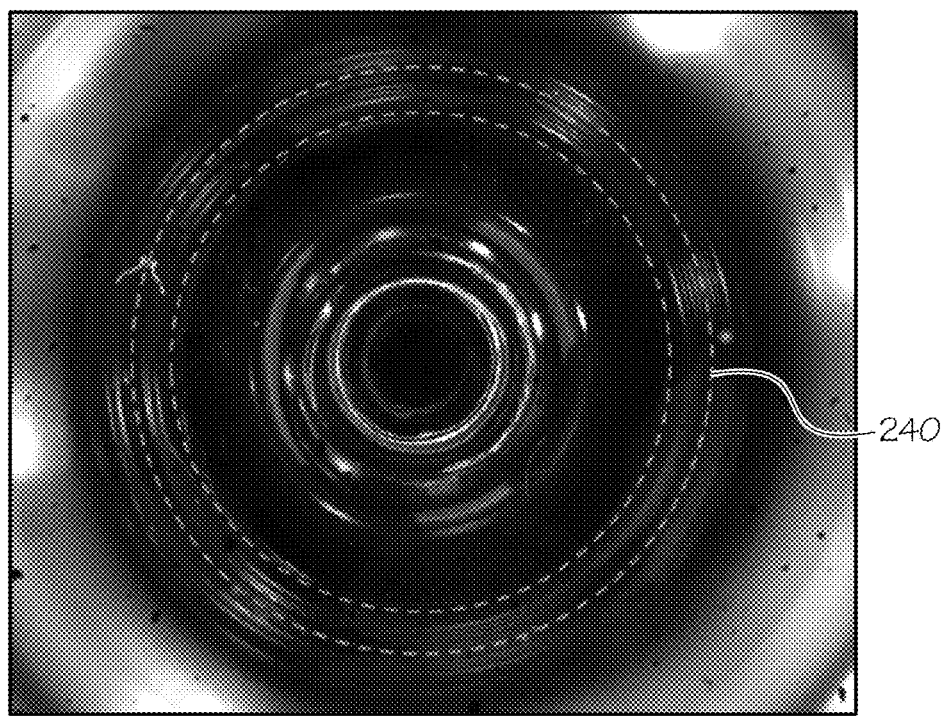
FIG. 4A illustrates an exemplary image captured by a camera without using a polarizer and an analyzer according to one or more embodiments described and shown herewith.
Figure 4B:
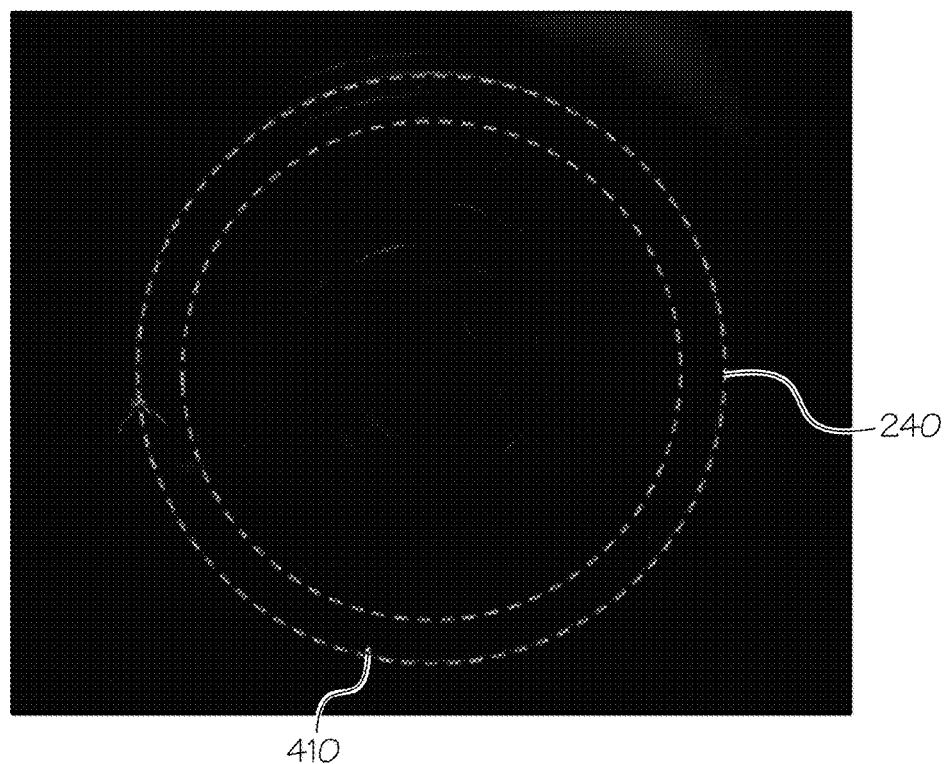
FIG. 4B illustrates an exemplary image captured by the camera using the polarizer and the analyzer according to one or more embodiments described and shown herewith.

FIGS. 4A and 4B illustrate comparison between an image captured by a particle detection system without using polarizers and an image captured by the present particle detection system using polarizers according to one or more embodiments shown and described herein. FIG. 4A illustrates an exemplary image captured by a camera without using the polarizer 130 and the analyzer 140. A light source may be located below the glass article 150 (e.g., located at −z direction from the glass article 150) and emit a ring light with a diffuser in a direction parallel to the longitudinal axis 190 of the glass article 150. The ring light lights up most of the glass article 150 as shown in FIG. 4A. Thus, it is difficult to detect particles on the glass article 150.

FIG. 4B illustrates an exemplary image captured by the camera 120 using the polarizer 130 and the analyzer 140 according to one or more embodiments shown and described herein. As described above, the polarization axis of the polarizer 130 is oriented orthogonal to the polarization axis of the analyzer 140. Thus, the polarizer 130 and the analyzer 140 working together effectively block reflections from the glass article 150 except for light scattered by particles on the glass article 150. The particle 410 may be identified as a white dot at the bottom of the region of interest 240. Because all the background is black but the particle 410, the particle 410 can be easily identified by human eyes or a processor such as the one or more processors 182.

FIGS. 5A and 5B schematically depict a glass particle detection system according to another embodiment shown and described herein. FIG. 5A depicts a partial side view of the glass particle detection system 500. The glass particle detection system 500 may include a light source 510, a camera 520, a glass article 530, an optical lens 540, and one or more rollers 550. The light source 510 may emit a light beam directed along a beam propagation axis 564. The light beam may be concentrated on a focal plane of the camera 520. Objects that are not on the focal plane may be poorly lit by the light source 510. The beam propagation axis 564 may be parallel with a longitudinal axis 560 of the glass article 530. In another embodiment, the beam propagation axis 564 may not be parallel with a longitudinal axis 560 of the glass article 530, but the beam propagation axis 564 may be crossed with the longitudinal axis at a point proximate to an inner wall 534 of the glass article 530.

The light source 510 may emit a coherent light beam using a dark field lighting technique. For example, the light source 510 may be a light source emitting a laser beam using a dark field lighting technique. The coherent light may be directed along the inner wall 534 of the glass article 530. Because the light source 510 uses a dark field lighting technique, light scattered by particles on the inner wall 534 is readily detectable by the camera 520, as will be described with reference to FIGS. 7A and 7B below. The light source 510 may be positioned such that its light beam illuminates any particles on the inner wall 534 of the glass article 530. This ensures that particles on the inner wall 534 are well-illuminated and minimizes the illumination of external particles, e.g., particles on the outer wall 532 of the glass article 530.

The camera 520 may be a line scan camera. The camera 520 may have a focal plane which overlaps with an inner wall 534 of the glass article 530. The camera 520 includes an optical lens 522. The optical lens 522 may have a depth-of-field that is approximately 75% of the thickness of the wall of the glass article 530. For example, the optical lens 522 may have approximately a 300 micrometer depth-of-field. The optical axis 562 of the camera 520 may be orthogonal to the beam propagation axis 564 of the light source 510 and the longitudinal axis 560 of the glass article 530. In another embodiment, the optical axis 562 may not be orthogonal to the beam propagation axis 564 of the light source 510. For example, an angle between the optical axis 562 and the beam propagation axis 564 may be less than 90 degrees.

The glass article 530 may have a cylindrical shape such as tubes, syringes, vials, etc. The glass article 530 has the longitudinal axis 560 which is parallel to the x axis of FIG. 5A. The glass article 530 may be placed on one or more rollers 550. The one or more rollers 550 rotate around their central axis 552 to rotate the glass article 530. As the glass article 530 rotates, the camera 520 may scan images throughout the inner wall 534. Once the glass article 530 rotates about 360 degrees, the camera 520 may process and synthesize the captured images to prepare a single integrated image that corresponds to the entire inner wall of the glass article 530. For example, by synchronizing the rotation of the glass article 530 and the frame capture of the glass article 530, an image of the inner wall 534 of the glass article 530 may be built up line-by-line. All the images corresponding to the inner wall 534 of the glass article 530 may be integrated to a full 2D representation of the 3D surface of the glass article 530. The camera 520 may communicate with the computing device 180 in a similar way as described with reference to FIG. 1. The optical lens 540 may be a collimating lens which collimates a light beam from the light source 510 to illuminate only the inner wall 534 of the glass article 530.

FIG. 5B depicts a front view of the glass particle detection system 500 according to one or more embodiments shown and described herein. In this embodiment, the glass article 530 is placed on two rollers 550. The two rollers 550 rotate around their central axis 552, and thereby rotating the glass article 530. The camera 520 may capture an image at a focal plane 570 of the camera 520. The two rollers 550 may rotate either clockwise or counterclockwise. Although two rollers are shown in FIG. 5B, more than two rollers or less than two rollers may be used to rotate the glass article 530.

Figure 6:
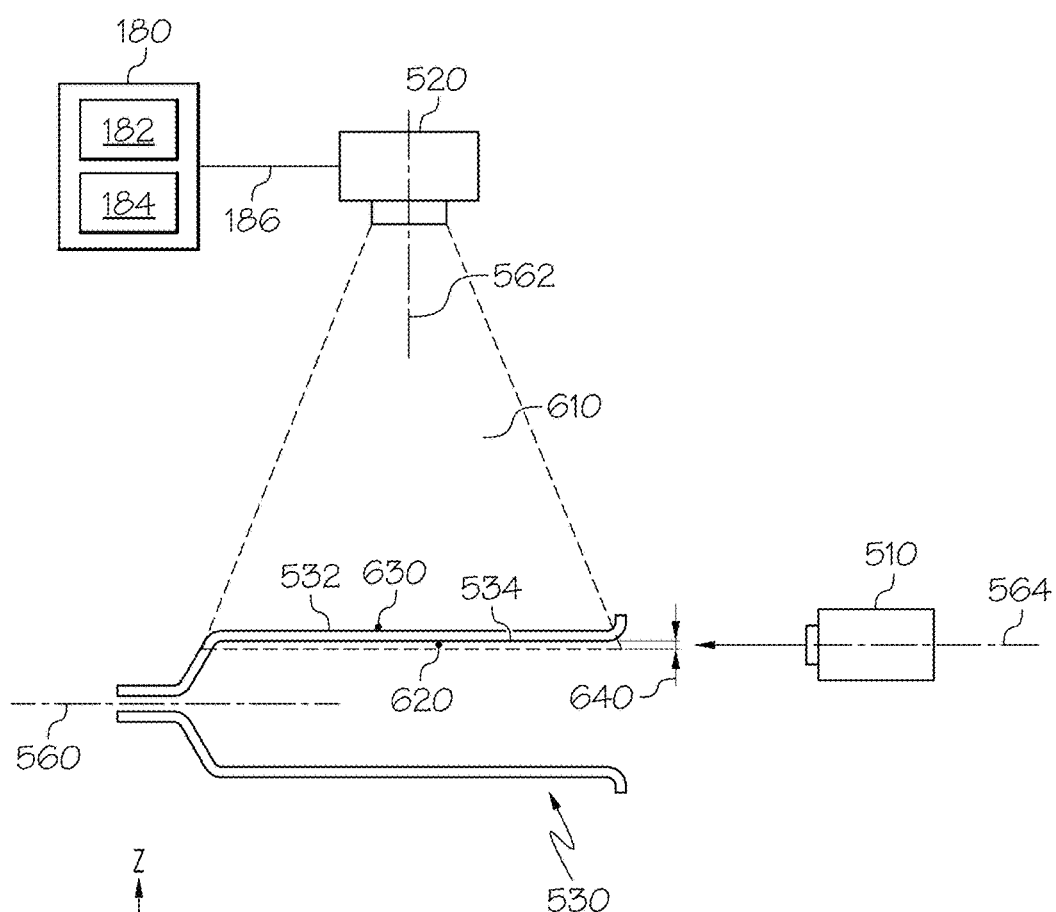
FIG. 6 depicts a camera configuration for determining the location of particles on a glass article according to one or more embodiments described and shown herewith.

FIG. 6 depicts camera configuration for determining the location of particles on a glass article according to one or more embodiments described and shown herewith. In this embodiment, an external particle 630 may be located on the outer wall 532 of the glass article 530, and an internal particle 620 may be located on the inner wall 534 of the glass article 530. The camera 520 may have a focal plane (not shown) which is located proximate to the inner wall 534 of the glass article 530. The camera 520 may have a field of view 610. The camera 520 may have a depth-of-field 640 which may be, e.g., less than 300 micrometers. In this embodiment, the internal particle 620 may be located within the focal plane of the camera 520 and the external particle 630 may be located outside the focal plane. In addition, the light source 510 may emit a collimating light illuminating the inner wall 534 of the glass article 530. Thus, an image of the external particle 630 captured by the camera 520 may be out of focus and poorly illuminated whereas an image of the internal particle 620 captured by the camera 520 may be in focus and well-illuminated.

The camera 520 may transmit the captured image to the computing device 180. The computing device 180 may determine whether the captured image includes particles in focus. If it is determined that the captured image includes particles in focus, the one or more processors 182 may determine that the particle is attached to the inner wall 534 of the glass article 530. The one or more processors 182 may indicate that the glass article 530 should be rejected based on the determination. The indication of rejection may be stored in the one or more memory modules 184 along with the identification of the glass article 530. If it is determined that the captured image does not include any particle in focus, the one or more processors 182 may determine that no particle is present on the inner wall 534 of the glass article 530. The determination may be stored in the one or more memory modules 184 along with the identification of the glass article 530.

Figure 7A:
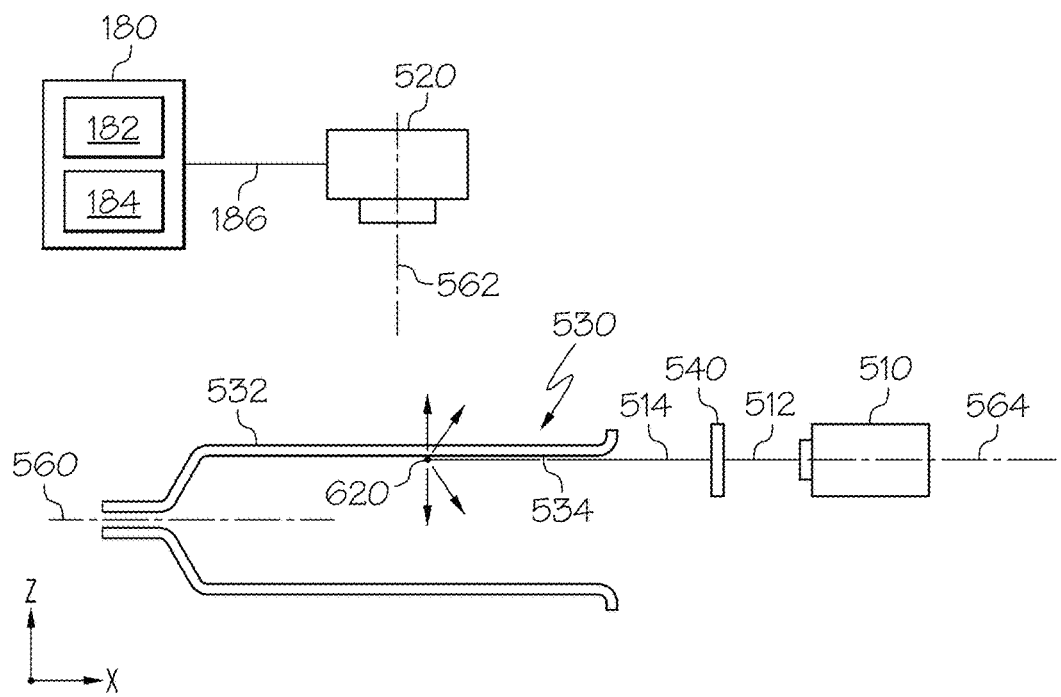
FIG. 7A depicts light scattered from an internal particle of a glass article according to one or more embodiments described and shown herewith.
Figure 7B:
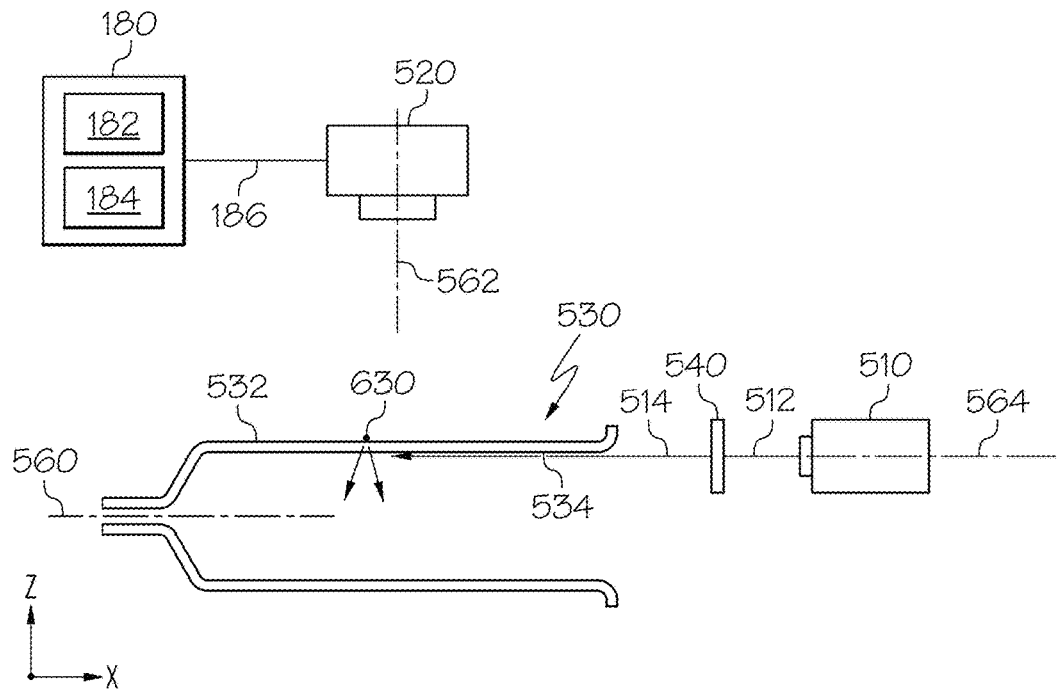
FIG. 7B depicts light scattered from an external particle of a glass article according to one or more embodiments described and shown herewith.

FIGS. 7A-7B depict light reflection on particles of a glass article according to one or more embodiments described and shown herewith. In FIG. 7A, the light source 510 may emit a light beam 512 along the beam propagation axis 564. The beam propagation axis 564 may be parallel with the longitudinal axis 560 of the glass article 530. The optical lens 540 may collimate the light beam 512 and emit a collimated light beam 514. The collimated light beam 514 illuminates the inner wall 534 of the glass article 530. The collimated light beam 514 is scattered by the internal particle 620 and a portion of the scattered light may be directed towards the camera 520 (+z direction). Thus, the camera 520 may capture the portion of the scattered light from the internal particle 620.

In FIG. 7B, the light source 510 may emit a light beam 512 along the beam propagation axis 564. The beam propagation axis 564 may be parallel with the longitudinal axis 560 of the glass article 530 and aligned with the wall of the glass article 530. The optical lens 540 may collimate the light beam 512 and output a collimated light beam 514. The collimated light beam 514 illuminates the inner wall 534 of the glass article 530. Because the external particle 630 is located on the outer wall 532 of the glass article 530, the collimated light beam 514 rarely reaches the external particle 630. In addition, even if a portion of the collimated light beam 514 reaches the external particle 630, the light reflected from the external particle 630 would not be directed toward the camera 520. In this regard, the camera 520 may capture scattered light only from particles located on the inner wall 534 of the glass article 530.

The camera 520 may transmit the captured image to the computing device 180. The computing device 180 may determine whether the captured image includes any particle. If it is determined that the captured image includes a particle, the one or more processors 182 may determine that the particle is attached to the inner wall 534 of the glass article 530. The one or more processors 182 may indicate that the glass article 530 should be rejected based on the determination. The indication of rejection may be stored in the one or more memory modules 184 along with the identification of the glass article 530. If it is determined that the captured image does not include any particle, the one or more processors 182 may determine that no particle is present on the inner wall 534 of the glass article 530. The determination may be stored in the one or more memory modules 184 along with the identification of the glass article 530.

Figure 8A:
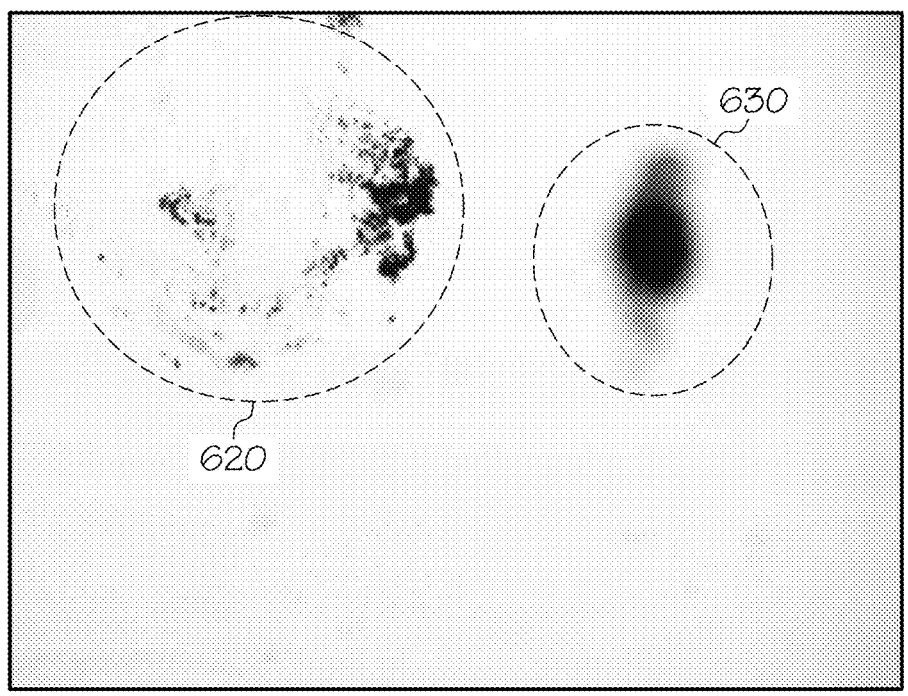
FIG. 8A depicts a sample image captured by a camera using conventional backlighting according to one or more embodiments described and shown herewith.
Figure 8B:
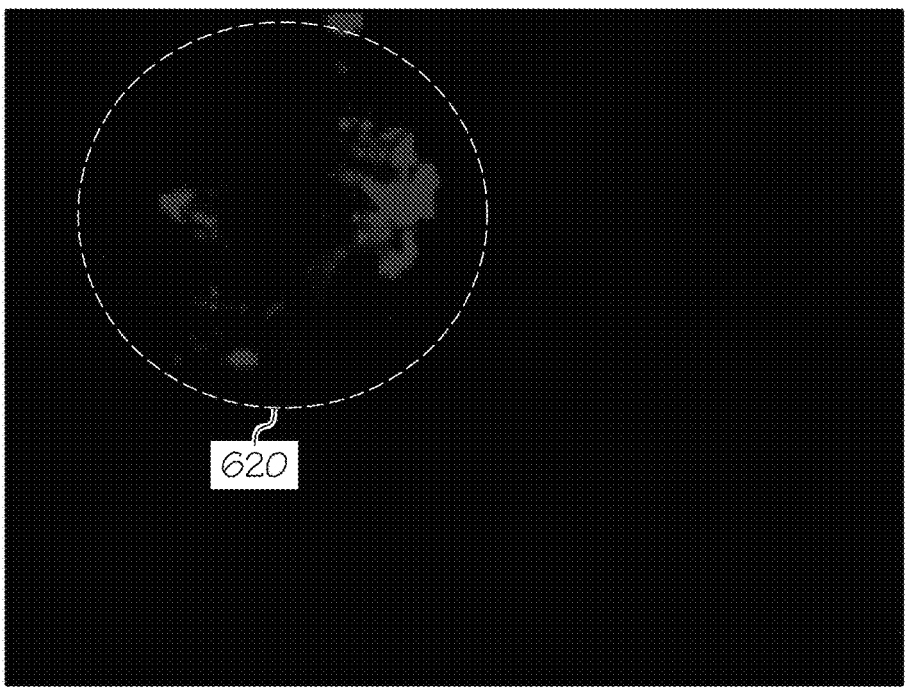
FIG. 8B depicts a sample image captured by a camera using the light source shown in FIG. 6 according to one or more embodiments described and shown herewith.

FIGS. 8A and 8B depict comparison between a captured image using a backlighting and a captured image using a laser dark field illumination. FIG. 8A depicts a sample image captured by a camera using a backlighting illuminating a glass article 530. In this example, the backlighting may be located below the glass article 530 (e.g., located at −z direction from the glass article 530). The glass article 530 includes both external particles 630 on the outer wall 532 and internal particles 620 on the inner wall 534. Both external particles 630 and the internal particles 620 are illuminated by the backlighting. The external particles 630 are captured by the camera 520 out of focus whereas the internal particles 620 are captured by the camera 520 in focus because only the internal particles 620 are located within the focal plane of the camera 520. However, it is difficult and takes time to distinguish the external particles from the internal particles on the sample image itself because the sample image includes illuminations from both the internal particles and the external particles.

FIG. 8B depicts a sample image captured by a camera using a light source which directs a light beam proximate to the inner wall 534 of the glass article 530 as shown in FIG. 5A. The light source 510 may be a light beam with laser dark field illumination. In this sample image of FIG. 8B, the internal particles 620 are well-lit whereas the external particles are not visible. Thus, in this sample image, it is much easier and convenient to determine whether internal particles 620 are present in a glass article. For example, the one or more processors 182 determines that the sample image of FIG. 8B includes particles 620, and determines that the particles 620 are attached to the inner wall 534 of the glass article 530. Then, the one or more processors 182 indicate that the glass article 530 should be rejected based on the determination.

Figure 9:
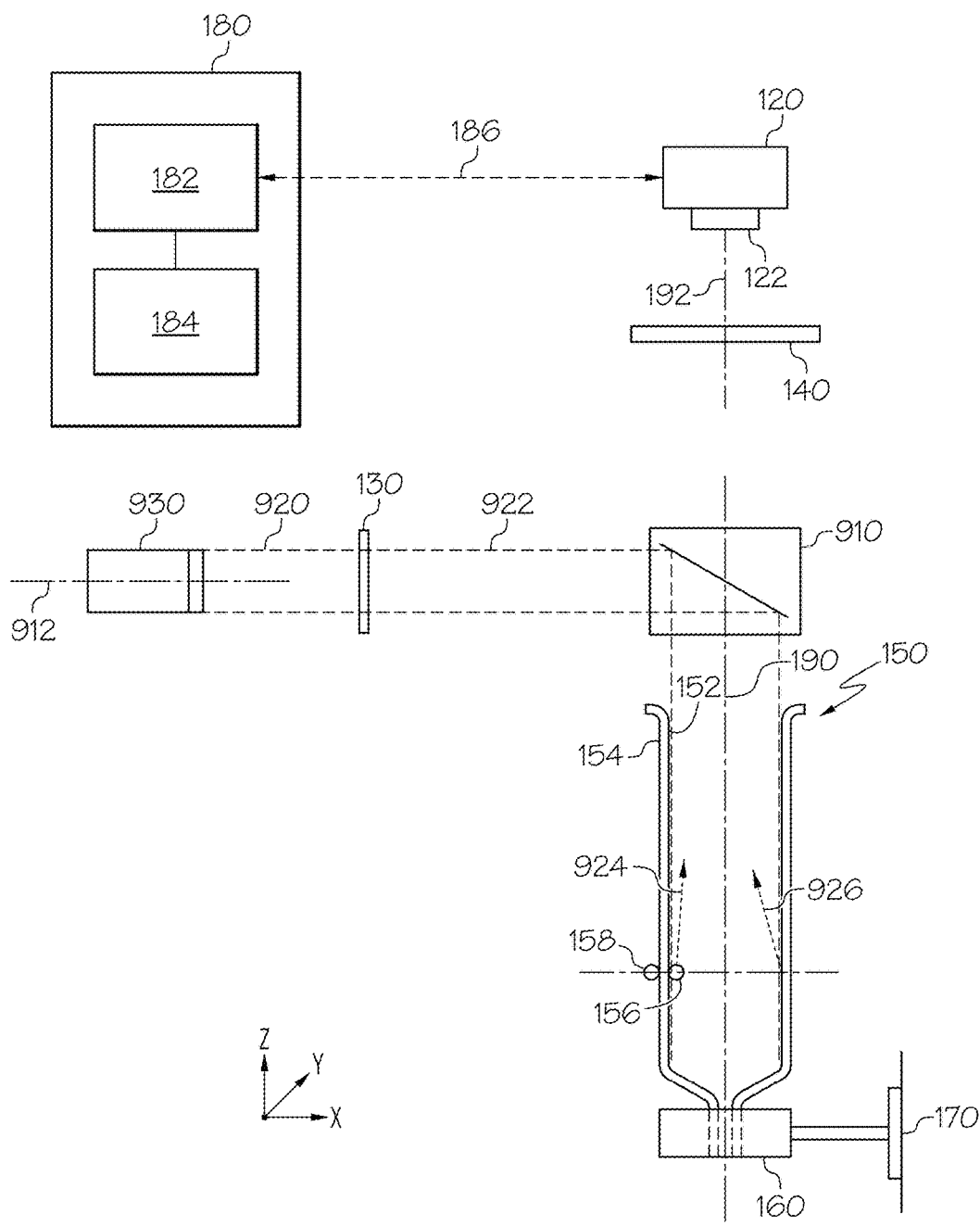
FIG. 9 schematically depicts a glass particle detection system according to one or more embodiments shown and described herein.

FIG. 9 schematically depicts a glass particle detection system according to another embodiment shown and described herein. The glass particle detection system includes a ring light source 930, a camera 120, a polarizer 130, an analyzer 140, a glass article 150, and a beam splitter 910. The glass article 150 may be a cylindrically-shaped glass such as a tube, a syringe, a vial, etc. The glass article 150 has a longitudinal axis 190 which is parallel with the z axis of FIG. 9. The glass article may be fixed to a holder 160 which is attached to a linear actuator 170.

The ring light source 930 may be a laser emitting a ring light 920 along the beam propagation axis 912. The beam propagation axis 912 may be parallel with the x axis of FIG. 9. The beam propagation axis 912 may be perpendicular to the longitudinal axis 190 of the glass article 150. In some embodiments, the beam propagation axis 912 may not be perpendicular to the longitudinal axis 190 of the glass article 150. For example, the angle between the beam propagation axis 912 and the longitudinal axis 190 may be less than 90 degrees. The diameter of the ring light 920 may be about the same as the diameter of the inner wall 152 of the glass article 150. The polarizer 130 may be positioned between the light source 110 and the beam splitter 910 such that the ring light 920 from the ring light source 930 passes through the polarizer 130 at a normal direction. The polarizer 130 polarizes the non-polarized ring light 920 according to the polarization axis of the polarizer 130 and outputs a polarized ring light 922. The polarized ring light 922 may produce less glare when reflecting on the glass article 150 compared to the non-polarized ring light 920.

The beam splitter 910 changes the propagation direction of the polarized ring light 922 and directs the polarized ring light 922 into the glass article 150 while still allowing the camera 120 to image the internal surface of the glass article 150. The outer diameter of the polarized ring light 922 may be matched to the diameter of the inner wall 152 of the glass article 150.

The glass article 150 may scatter the polarized ring light 922. If the glass article 150 includes any particles, the polarized ring light 922 may be scattered by the particles. The polarization direction of the polarized ring light 922 is changed when the polarized ring light 922 is scattered by the particles. In this embodiment, the glass article 150 may have an internal particle 156 attached on the inner wall 152 of the glass article 150 and an external particle 158 attached on the outer wall 154 of the glass article 150. The polarized ring light 922 is scattered by the internal particle 156. In contrast, the polarized ring light 922 is not scattered by the external particle 158 because the polarized ring light 922 may not reach the external particle 158.

The polarization direction of the scattered light may be changed. For example, the polarized ring light 922 that was scattered by the internal particle 156 is polarized in a direction that is different from the polarization direction of the polarized ring light 922. In contrast, the polarization direction of the polarized ring light 922 is not changed when it reflects on the glass article 150 where no particle is present at the reflection region. For example, the light 926 which was reflected from the glass article 150 is polarized in the same direction as the polarized ring light 922.

In contrast, the polarized ring light 922 from the ring light source 930 may not be scattered by the external particle 158 because the polarized ring light 922 may rarely reach the external particle 158. In addition, even if a portion of the polarized ring light 922 reaches the external particle 158, the light reflected from the external particle 158 would not be directed toward the camera 120.

The analyzer 140 is positioned between the beam splitter 910 and the camera 120. The analyzer 140 may be a polarizer that polarizes an incident light. The analyzer 140 may have similar light optical characteristics (e.g., polarization) as the polarizer 130. The polarization axis of the analyzer 140 may be oriented to a different direction than the polarization axis of the polarizer 130. For example, the polarization axis of the analyzer 140 may be oriented at about ±90 degrees relative to the polarization axis of the polarizer 130. Thus, the ring light 922 polarized according to the polarization axis of the polarizer 130 cannot pass through the analyzer 140 because the ring light 922 is polarized in a direction orthogonal to the polarization axis of the analyzer 140. Similarly, the light 926 which was reflected from the glass article 150 cannot pass through the analyzer 140 because the light 926 is polarized in a direction orthogonal to the polarization axis of the analyzer 140.

In contrast, the light 924 that was scattered by the internal particle 156 is polarized in a direction that is not orthogonal to the polarization axis of the polarized ring light 922. For example, if the ring light 922 is polarized according to the polarization axis of the polarizer 130, the polarization direction of the light 924 may be different from the polarization axis of the polarizer 130, but not orthogonal to the polarization axis of the analyzer 140. Thus, a portion of the light 924 would pass through the analyzer 140 because the difference between the polarization direction of the light 924 and the polarization axis of the analyzer 140 is not 90 degrees, i.e., not orthogonal. In this regard, only light that is scattered by particles on the inner wall 152 of the glass article 150 can pass through the analyzer 140.

Figure 10:
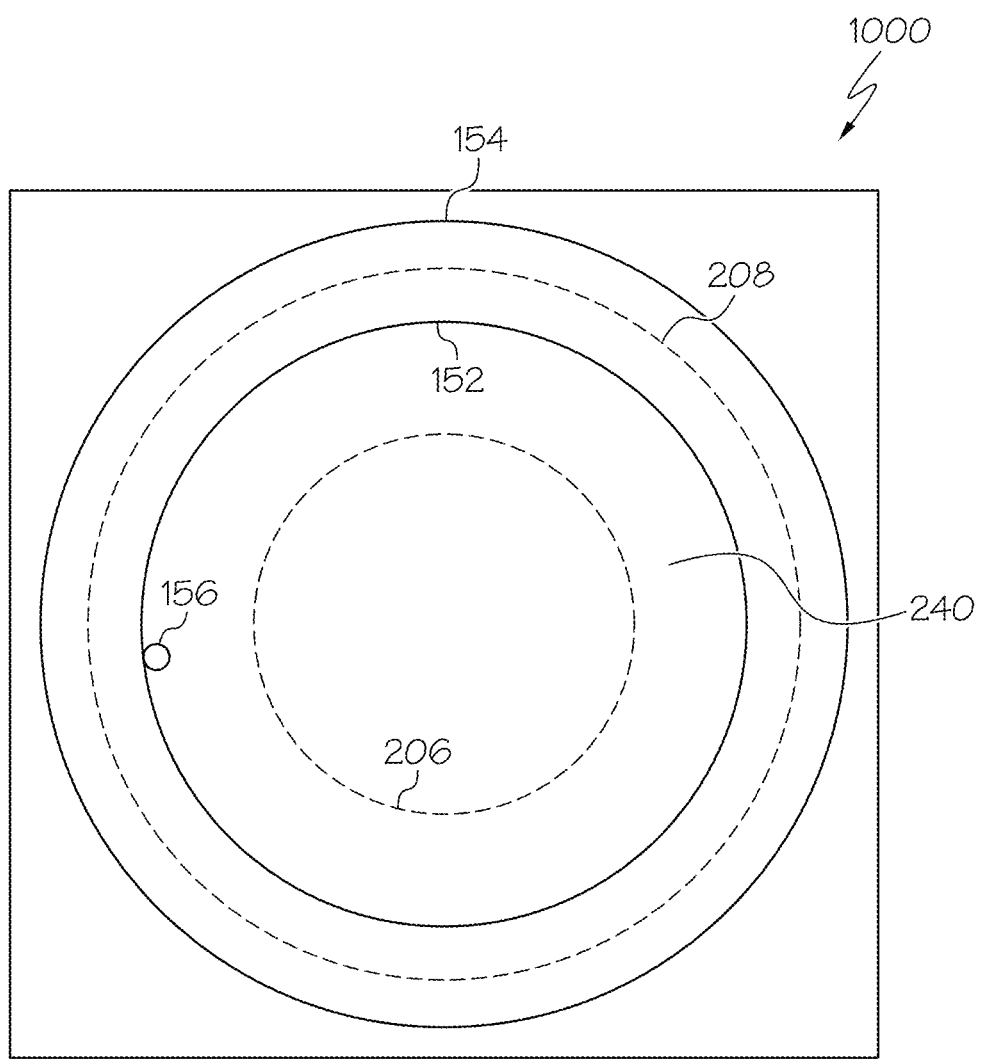
FIG. 10 depicts an image of a ring light reflected from the glass article according to one or more embodiments described and shown herewith.

The camera 120 may capture an image of the ring light reflected from the glass article 150. The camera 120 may be any device having an array of sensing devices capable of detecting radiation in an ultraviolet wavelength band, a visible light wavelength band, or an infrared wavelength band. The camera 120 may have a focal plane that may be parallel to the x-y plane of FIG. 9 and cross the glass article 150. The camera 120 may include an optical lens 122. The optical axis of the camera may be perpendicular to the beam propagation axis 912. The optical axis 192 of the camera 120 may be parallel with the longitudinal axis 190 of the glass article 150. In some embodiments, the optical axis 192 of the camera 120 may be co-located with the longitudinal axis of the glass article 150. In another embodiment, the optical axis 192 of the camera 120 may not be parallel with the longitudinal axis 190 of the glass article 150, but the optical axis 192 may be crossed with the longitudinal axis 190 of the glass article at a point proximate to the focal plane of the camera 120. The camera 120 may capture an image of the ring light on the focal plane which, for example, includes the internal particle 156 as illustrated in FIG. 10. The camera 120 may communicate with the computing device 180 in a similar way as described with reference to FIG. 1.

The linear actuator 170 may move in a vertical direction (+/−z direction) to move the glass article 150 in the vertical direction. As the linear actuator 170 moves glass article 150 in the vertical direction, the focal plane of the camera 120 may be placed on different cross-sections of the glass article 150 in terms of the vertical direction (+/−z direction). Thus, the camera 120 can capture images of the ring light reflected from each and every wall of the glass article 150.

FIG. 10 depicts an image of the ring light reflected from the glass article. In this embodiment, the image 1000 illustrates a view of a focal plane of the camera 120. The image 1000 may depict the inner wall 152 and the outer wall 154 of the glass article 150, a region of interest 240, and an internal particle 156.

The outer wall 154 and the inner wall 152 may be illustrated in the image 1000 in FIG. 10 for reference only, and the actual image may not include the outer wall 154 and the inner wall 152. As described above, because the polarization direction of the ring light scattered by the internal particle 156 is changed, the light scattered by the internal particle 156 can pass through the analyzer 140 and reach the camera 120. Thus, the internal particle 156 may be visible to the camera 120. In contrast, the external particle 158 is not shown in the image 1000 because the polarized ring light 922 is rarely scattered by the external particle 158 as discussed above. In this regard, the image 1000 may only capture particles on the inner wall 152 of the glass article 150.

The indication of the region of interest 240 may be embedded to the image 1000 in order to facilitate determining whether a particle is present on the inner wall of the glass article 150. In embodiments, the one or more processors 182 may determine whether any particle is present within the region of interest 240 of the image captured by the camera 120. If it is determined that a particle is present within the region of interest 240, the one or more processors 182 may determine that the particle is attached to the inner wall of the glass article 150. The one or more processors 182 may indicate that the glass article 150 should be rejected based on the determination. The indication of rejection may be stored in the one or more memory modules 184 along with the identification of the glass article 150. If it is determined that no particle is present within the region of interest 240, the one or more processors 182 may determine that no particle is present on the inner wall of the glass article 150. The determination may be stored in the one or more memory modules 184 along with the identification of the glass article 150.

According to one or more embodiments of the present disclosure, the combination of the lighting and optics geometry allows for accurate detection of internal particles of a glass article. The light and optics geometry produces a virtual image of a particle as shown in FIGS. 3A and 3B, which not only increases particle detectability but also enhances accuracy of determination whether a particle is attached on the inner wall of a glass article. In addition, with the lighting optics geometry, the detection of particles on inner walls of glass articles may be automated. For example, 80 glass articles per minute can be examined whether they have particles on inner walls of glass articles. The present light and optics geometry may be used for different sizes and dimensions of glasses. For example, the present method may be applied to glass articles with different thicknesses and/or shapes. Furthermore, because the present detection systems focus on detecting particles on the inner walls of glass articles and reject those glass articles with internal particles, glass articles that only include external particles are not rejected altogether in the process of testing glass articles. Thus, the present detection method improves glass article yield and saves costs.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an" and "the" include plural referents unless the context clearly dictates otherwise. Thus, for example, reference to "a" component includes aspects having two or more such components, unless the context clearly indicates otherwise.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A glass particle detection system, comprising:
 a light source configured to emit a light beam into a cylindrical glass article when the cylindrical glass article is imaged by the glass particle detection system, the light beam being directed along a beam propagation axis that is perpendicular to a longitudinal axis of the cylindrical glass article;
 a polarizer positioned between the light source and the cylindrical glass article;
 a camera configured to capture an image of the light beam reflected from the cylindrical glass article, an optical axis of the camera being perpendicular to the beam propagation axis of the light source;
 an analyzer positioned between the cylindrical glass article and the camera; and
 a computing device communicatively coupled to the camera, the computing device comprising at least one processor and at least one memory storing computer readable and executable instructions that, when executed by the at least one processor, cause the computing device to:
  determine boundaries of an inner wall and an outer wall of the cylindrical glass article based on the captured image;
  determine a region of interest based on the boundaries; and
  determine whether a particle is present within the region of interest.

2. The glass particle detection system of claim 1, wherein a polarization axis of the polarizer is oriented at about 90 degrees relative to a polarization axis of the analyzer.

3. The glass particle detection system of claim 1, wherein the light source is a laser light source.

4. The glass particle detection system of claim 1, further comprising:
 a holder for holding the cylindrical glass article; and
 an actuator coupled to the holder and configured to move the holder in a direction parallel to the longitudinal axis of the cylindrical glass article.

5. The glass particle detection system of claim 1, wherein the computer readable and executable instructions, when executed by the processor, cause the computing device to determine that a particle is attached to the inner wall of the cylindrical glass article if it is determined that the particle is present within the region of interest.

6. The glass particle detection system of claim 1, wherein the computer readable and executable instructions, when executed by the processor, cause the computing device to determine that no particle is attached to the inner wall of the cylindrical glass article if it is determined that no particle is present within the region of interest.

7. The glass particle detection system of claim 1, wherein the region of interest is defined by an inner circle and an outer circle,
 a center of the inner circle is the same as a center of the outer circle,
 a radius of the outer circle is less than a radius of the outer wall of the cylindrical glass article and more than a radius of the inner wall of the cylindrical glass article, and
 a radius of the inner circle is less than a radius of the inner wall of the cylindrical glass article.

8. The glass particle detection system of claim 7, wherein the radius of the inner circle is between about 90% of the radius of the inner wall and about 95% of the radius of the inner wall.

9. A method for detecting particles on a cylindrical glass article, comprising:
 directing a light beam through a polarizer into the cylindrical glass article along a beam propagation axis that is perpendicular to a longitudinal axis of the cylindrical glass article, the light beam polarized by the polarizer producing light scattered by one or more particles on the inner wall of the cylindrical glass article;
 capturing, by a camera having an optical axis perpendicular to the beam propagation axis, an image of the light beam reflected from the cylindrical glass article including the scattered light via an analyzer, the analyzer located between the cylindrical glass article and the camera, and a polarization axis of the polarizer being oriented at about 90 degrees relative to a polarization axis of the analyzer;
 determining boundaries of the inner wall and an outer wall of the cylindrical glass article on the image;
 determining a region of interest based on the boundaries;
 processing the image to filter out illumination outside the region of interest; and
 determining whether a particle is present within the region of interest.

10. The method of claim 9, further comprising
 determining that a particle is attached to the inner wall of the cylindrical glass article if it is determined that the particle is present within the region of interest.

11. The method of claim 9, further comprising
 determining that no particle is attached to the inner wall of the cylindrical glass article if it is determined that no particle is present within the region of interest.

12. The method of claim 9, wherein the region of interest is defined by an inner circle and an outer circle,
 a center of the inner circle is the same as a center of the outer circle,
 a radius of the outer circle is less than a radius of an outer wall of the cylindrical glass article and more than a radius of an inner wall of the cylindrical glass article, and
 a radius of the inner circle is less than a radius of the inner wall of the cylindrical glass article.

13. The method of claim 9, wherein the optical axis of the camera is parallel with the longitudinal axis of the cylindrical glass article.

14. The method of claim 9, further comprising
 moving, by an actuator, the cylindrical glass article in a direction parallel to the longitudinal axis of the cylindrical glass article.

* * * * *